United States Patent [19]

Low et al.

[11] 4,395,404
[45] Jul. 26, 1983

[54] SYNTHETIC THYMOSIN $\beta_3$ AND $\beta_4$ ANALOGUES

[75] Inventors: Teresa L. K. Low, Annandale, Va.; Allan L. Goldstein, Washington, D.C.

[73] Assignee: George Washington University, Washington, D.C.

[21] Appl. No.: 378,463

[22] Filed: May 14, 1982

[51] Int. Cl.³ .................... A61K 37/00; C07C 103/52
[52] U.S. Cl. ............................. 424/177; 260/112.5 R
[58] Field of Search ................. 424/177; 260/112.5 R

[56] References Cited

U.S. PATENT DOCUMENTS 4,261,886  4/1981  Goldstein et al. ........... 260/112.5 R Primary Examiner—Delbert R. Phillips
Attorney, Agent, or Firm—Jon S. Saxe; George M. Gould; Peter R. Shearer

[57] ABSTRACT

Novel peptides representing fragments of thymosin $\beta_3$ and $\beta_4$ have been synthesized and are active agents affecting regulation, differentiation and function of thymus dependent lymphocytes and macrophages.

13 Claims, No Drawings

SYNTHETIC THYMOSIN $\beta_3$ AND $\beta_4$ ANALOGUES

BACKGROUND OF THE INVENTION

Several peptide factors present in the thymus gland have been implicated to play important roles in the development and maintenance of immunological competence in man and in animals. The importance of the immune system in the defense against cancer and tumor cells is now widely recognized. In recent years, a few polypeptides shown to be able to stimulate maturation, differentiation and function of T cells have been isolated from bovine thymus. Among them, the acidic peptide thymosin $\alpha_1$, has been intensively studied. Its structure and activity have been described in U.S. Pat. No. 4,079,127.

Additionally, Goldstein et al. J. of Reticuleondothelial Society 23, 253 (1978) describe partially purified thymosin $\beta_3$ and $\beta_4$ as components of the partially purified thymosin fraction 5. Low and Goldstein in Year in Hematology 1978, Siber et al. ed (Plenum Pub. Co. 1978) at p. 281 indicated that partially purified thymosin $\beta_3$ and $\beta_4$ induce TdT positive cells in T-cell populations. It has also been reported that thymosin $\beta_3$ and $\beta_4$ accelerate the reappearance of TdT positive cells in the thymus following steroid induced immunosuppression [Low, et al. PNAS 78, 1162 (1981); Mol. Cell. Biochem. 41, 49 (1981)], and inhibit the migration of macrophages [Thurman et al., Lymphokines and Thymic Hormones: Their Potential Utilization in Cancer Therapeutics, Goldstein & Chirigos (eds), Raven Press, p. 145 (1981)].

Furthermore in the course of synthesizing thymosin $\alpha_1$ by solution phase methodology, Wang in U.S. Pat. No. 4,148,788 utilized the protected carboxyl terminal octa-, undeca- and tetradecapeptides of thymosin $\alpha_1$ as intermediates. These compounds were also deprotected by hydrogenolysis followed by treatment with HF and the resulting free peptides were indicated to have activity in the regulation, differentiation and function of T-cells.

SUMMARY OF THE INVENTION

The present invention relates to novel peptides of the formula:

R-Gly-Glu-Ser-R₁  I wherein R represents H-Q,Q-Ala-, Q-Gln-Ala, H-Lys-Gln-Ala, Q-Glu-Lys-Gln-Ala-, Q-Gln-Glu-Lys-Gln-Ala-, Q-Glu-Gln-Glu-Lys-Gly-Ala-, Q-Ile-Glu-Gln-Glu-Lys-Gin-Ala-, Q-Thr-Ile-Glu-Gln-Glu-Lys-Gln-Ala-, Q-Glu-Thr-Ile-Glu-Gln-Glu-Lys-Gin-Ala-, or wherein Q represents H or acyl; and R₁ represents -OH, -A-C or -A-B-C wherein A represents Asp or Asn, B represents -Glu-Ile-Thr- and C represents -Ala-Lys-Thr-OH.
and the pharmaceutically acceptable acid or base addition salts thereof.

More particularly the peptides of formula I include peptides having the following amino acid sequences:

II

H-Glu-Thr-Ile-Glu-Gln-Glu-Lys-Gln-Ala-Gly-Glu-Ser-OH.

III

H-Thr-Ile-Glu-Gln-Glu-Lys-Gln-Ala-Gly-Glu-Ser-OH

IV

H-Ile-Glu-Gln-Glu-Lys-Gln-Ala-Gly-Glu-Ser-OH.

V

H-Glu-Gln-Glu-Lys-Gln-Ala-Gly-Glu-Ser-OH.

VI

H-Gln-Glu-Lys-Gln-Ala-Gly-Glu-Ser-OH.

VII

H-Glu-Lys-Gln-Ala-Gly-Glu-Ser-OH.

VIII

H-Lys-Gln-Ala-Gly-Glu-Ser-OH.

IX

H-Gln-Ala-Gly-Glu-Ser-OH.

X

H-Ala-Gly-Glu-Ser-OH.

XI

H-Gly-Glu-Ser-OH.

XII

H-Gln-Ala-Gly-Glu-Ser-Asp-Ala-Lys-Thr-OH.

XIII

H-Gln-Ala-Gly-Glu-Ser-Asn-Ala-Lys-Thr-Oh.

XIV

CH₃CO-Gln-Sar-Gly-Glu-Ser-Asp-Ala-Lys-Thr-OH.

XV

CH₃CO-Gln-Sar-Gly-Glu-Ser-Asn-Ala-Lys-Thr-Oh.

XVI

H-Gln-Ala-Gly-Glu-Ser-Asp-Glu-Ile-Thr-Ala-Lys-Thr-OH.

These peptides of the invention are useful in methods for stimulating the production of TdT positive prothymocytes.

DESCRIPTION OF THE INVENTION

The present invention relates to novel peptides which relate to the sequence of the carboxyl terminal of the known immunostimulatory thymic peptides thymosin $\beta_3$ and $\beta_4$. The peptides of this invention can be conveniently represented by formula I.

Acyl as described in formula I may be selected from various residues of known aliphatic acids having from 1-7 carbon atoms. In the preferred embodiment of this invention, acyl represents an acetyl residue from acetic acid.

Compounds of formula I may be readily synthesized by any known conventional procedure for the formation of a peptide linkage between amino acids. Such conventional procedures include for example any solution phase procedure permitting a condensation reaction between the free alpha amino group of an amino acid or residue thereof having its carboxylic group or other reactive groups protected and the free primary carboxylic group of another amino acid or residue thereof having its amino group or other reactive groups protected.

The process for synthesizing compounds of formula I may be carried out by a procedure whereby each amino acid in the desired sequence is added singly successively to another amino acid or residue thereof or by a procedure whereby peptide fragments with the desired amino acid sequence are first synthesized conventionally and then condensed to provide the desired peptide.

Such conventional procedures for synthesizing compounds for formula I include also for example any automatic solid phase synthesis method. In such a method the synthesis of compounds of formula I can be carried out by sequentially incorporating the desired amino acid residues one at a time into the growing peptide chain according to the general principles of solid phase methods [Merrifield, R. B., J. Am. Chem. Soc. 85, 2149-2154 (1963); Barany et al, The Peptides, Analysis, Synthesis and Biology, Vol. 2, pp 1-284, (1980)].

In the preferred aspect of the present invention, compounds II-XI of formula I are prepared by solid phase peptide synthesis. In such embodiment commercially available chloromethylpolystyrene resin is acylated with Nα-Boc-O-benzyl-L-serine in the presence of dicyclohexyl-carbodiimide (DCC) to give Boc-O-benzyl-L-seryl resin. This amino acid resin is placed into the reaction vessel of an automated solid phase peptide synthesis apparatus. The apparatus is then programmed to perform the solid phase synthesis to incorporate the following amino acid unit in each cycle sequentially beginning with Boc-Glu (OBzl)-OH:

(1) Boc-Gly-OH (stop synthesis for tripeptide of formula XI)

(2) Boc-Ala-OH (stop synthesis for tetrapeptide of formula X)

(3) Boc-GlnONp (stop synthesis for pentapeptide of formula IX)

(4) Boc-Lys(Z)-OH (stop synthesis for hexapeptide of formula VIII)

(5) Boc-Glu(OBzl)-OH (stop synthesis for heptapeptide of formula VII)

(6) Boc-GlnONp (stop synthesis for octapeptide of formula VI)

(7) Boc-Glu(OBzl)-OH (stop synthesis for nonapeptide of formula V)

(8) Boc-Ile-OH (stop synthesis for decapeptide of formula IV)

(9) Boc-Thr(OBzl)-OH (stop synthesis for undecapeptide of formula III)

(10) Boc-Glu(OBzl)-OH (stop synthesis for dodecapeptide of formula II)

wherein Boc represents t-butyloxycarbonyl, OBzl represents benzyl ester, ONp represents para-nitrophenyl ester and Z represents benzyloxycarbonyl.

It is recognized that other variations may conventionally be employed in the amino acid units being incorporated in each cycle, i.e. items 1-10 above. For example, Boc-Gln-ONp (item 3 above), Boc-Lys (Z)-OH (item 4 above) and Boc-Gln-ONp (item 6 above) may be replaced by Boc-Gln-OH, Boc-Lys(2-ClZ)-OH, and Boc-Gln-OH, respectively. Such replacements would permit synthesis of compounds II-XI of formula I by a solid phase peptide synthesis procedure analogous to that procedure disclosed in Wang, et al, Int. J. Peptide Protein Res. 18, 413-415 (1981). In the case of Boc-Gln-OH preactivation is carried out at 0° C. from 20 min by addition of DCC and hydroxybenzotriazole (HOBt). The dicyclohexylurea is removed by filtration and the resulting active ester is added to the growing peptide resin.

In the preferred aspect of the present invention, compounds XII-XVI of formula I are prepared by solid phase peptide synthesis. In such embodiment commercially available chloromethyl polystyrene resin is acylated with Nα-Boc-O-benzyl-L-threonine in the presence of DCC to give Boc-O-benzyl-L-threonyl resin. This amino acid resin is placed into the reaction vessel of an automated solid phase peptide synthesis apparatus. The apparatus is then programmed to perform the solid phase synthesis to incorporate the following amino acid unit in each cycle sequentially as shown below in each column designated A-E in Table I:

TABLE I

| (A) | (B) | (C) | (D) | (E) |
|---|---|---|---|---|
| Boc—Lys(Z)—OH | same | same | same | same |
| Boc—Ala—OH | same | same | same | same |
| Boc—Asp(OBzl)—OH | Boc—Asn—ONp | Boc—Asp(OBzl)—OH | Boc—Asn—ONp | Boc—Thr(OBzl)—OH |
| Boc—Ser(OBzl)—OH | same | same | same | Boc—Ile—OH |
| Boc—Glu(OBzl)—OH | same | same | same | same |
| Boc—Gly—OH | same | same | same | Boc—Asp(OBzl)—OH |
| Boc—Ala—OH | same | Boc—Sar—OH | same | Boc—Ser—(OBzl)—OH |
| Boc—Gln—ONp (stop synthesis for nonapeptide of formula XII) | same (stop synthesis for nonapeptide of formula XIII) | CH₃CO—Gln—ONp (stop synthesis for nonapeptide of formula XIV) | same (stop synthesis for nonapeptide of formula XV) | Boc—Glu(OBzl)—OH |
| | | | | Boc—Gly—OH |
| | | | | Boc—Ala—OH |
| | | | | Boc—Gln—ONp (stop synthesis for dodecapetide of formula XVI) |

Four fold excess of each Boc-amino acid and DCC can be used in each coupling reaction (120 minutes) and a 30 minute treatment with 33% trifluoroacetic acid in methylene chloride can be used as deprotecting agent for the Boc-group. The respective protected peptide resins thus obtained are then treated with anhydrous HF-anisole to remove all the side chain protecting groups and at the same time to release the unprotected peptide from the resin. The crude peptides may be desalted on a Sephadex G-10 column and then purified by column chromatography, i.e., DEAE-Sephadex A-25.

While specific protecting groups have been disclosed in regard to the solid phase synthesis aspect, it should be noted that each amino acid can be protected by any protective groups conventionally used for the respective amino acids in solution phase synthesis. Among such protecting groups there are included for example conventional protecting groups for carboxyl groups selected from esters such as aryl esters, particularly phenyl or phenyl substituted with lower alkyl, halo nitro, thio or substituted thio, i.e., lower alkyl (1-7 carbon atoms) thio and the like. While any conventional amino or amino protecting group such as butyloxycarbonyl (Boc) or benzyloxycarbonyl may be used. The conventional protecting group for the hydroxyl groups of serine residue may be selected from conventional carboxyl protecting groups such as those listed above.

The compounds of formula I of the present invention have activity in the regulation, differentiation and function of T-cells. Such activity must be considered unexpected in view of the knowledge in the peptide hormone art that the deletion of even one amino acid from the sequence of a biologically active peptide can result in the loss of biological activity. This is particularly true for relatively small peptide molecules.

Particularly the compounds of formula I are inducers of the non-template directed DNA polymerase known as "terminal deoxynucleotidyl transferase" (TdT). Furthermore, compounds of formula I act as glucocorticoid antagonists to counteract in vivo the effects of glucocorticoids, such as hydrocortisone acetate (HCA), on the thymus and immune system by accelerating the reconstitution of thymocyte populations within the thymus and of TdT positive thymocytes. The compounds of formula I are also capable of non-specifically inhibiting the migration of macrophages in the absence of specific antigen as determined by an in vitro macrophage migration inhibition factor (MIF) assay. Furthermore compounds of formula I are capable of restoring immunological responses in steroid suppressed mammals.

The compounds of formula I may be administered to warm-blooded mammals by parenteral application either intravenously, subcutaneously or intramuscularly. These compounds are potent immunopotentiating agents with a daily dosage in the range of about 0.1 to 50 mg/kg of body weight per day for intravenous administration. Obviously, the required dosage will vary with the particular condition being treated, the severity of the condition and the duration of treatment. A suitable dosage form for pharmaceutical use is 1 to 5 mg of lyophilized compound of formula I to be reconstituted prior to use by the addition of sterile water or saline.

Also indicated within the scope of the present invention are the pharmaceutically acceptable salts of the compounds of formula I. Suitable salts include sodium, potassium or a strong organic base such as guanidine. In addition, the counter ions of these cations, such as the chloride, bromide, sulfate, phosphate, malate, ascorbate and the like, may be included in the preparation.

The present invention is further illustrated by the Examples which follow.

EXAMPLE 1

Glycyl-L-glutamyl-L-serine (XI)

A solution of 3.511 g (11.9 mmol) of Nα-Boc-O-benzyl-L-serine, 1.50 ml (10.7 mmol) of triethylamine in 25 ml of absolute ethanol is reacted with 10.0 g (11.9 mmol) of chloromethylated copolystyrene-1% divinylbenzene (1.19 mmol Cl/g resin). The reaction mixture is stirred at reflux for 48 hours (hr), filtered and washed three times each with ethanol, H$_2$O, methanol and CH$_2$Cl$_2$ and dried in vacuo. Deprotection by carrying out steps a-d below gives TFA-H-Ser(B-1)-O-Resin. Amino acid analysis shows the resin to contain 0.271 mmol of ser/g.

The reaction time for each coupling is 2 hr. One cycle of the synthesis consists of: (a) methylene chloride (3 times for 5 min); (b) 33% trifluoroacetic acid-methylene chloride (2 min); (c) 33% trifluoroacetic acid-methylene chloride (30 min); (d) methylene chloride (3 times for 5 min); (e) 5% diisopropylethylamine-methylene chloride (2 min); (f) 5% diisopropylethylamine-methylene chloride (10 min); (g) methylene chloride (3 times for 5 min); (h) DMF (3 times for 5 min); (i) methylene chloride (3 times for 5 min); (j) Boc-amino acid (10 min) followed by (k) DCC (2 hrs); (l) methylene chloride (3 times for 5 min); (m) isopropanol (3 times for 5 min) and (n) DMF (3 times for 5 min).

A 10.0 g portion of the TFA-H-Ser(Bzl)-O-Resin (2.71 mmol) is coupled respectively by 1 cycle each with Boc-Glu(OBzl)-OH (3.65 g, 10.84 mmol, 4 equiv.) and Boc-Gly-OH (2.05 g, 10.84 mmol, 4 equiv.) to give the tripeptide-resin.

A 1.0 g portion (0.271 mmol) of the tripeptide-resin is cleaved at 0° for 45 min. with HF (~10 ml) containing anisole (1.5 ml, 13.6 mmol, 50 equiv.) The HF is removed in vacuo and the residue washed with ether, extracted into 0.1 M acetic acid and lyophilized to give a white solid, the compound of formula XI.

EXAMPLE 2

L-Alanyl-glycyl-L-glutamyl-L-serine(X)

The remainder of the tripeptide resin (2.439 mmol) is coupled by 1 cycle with Boc-Ala-OH (1.85 g, 9.76 mmol, 4 equiv) to give the tetrapeptide-resin.

A 1.0 g portion (0.271 mmol) of the tetrapeptide resin is cleaved at 0° for 45 min. with HF (~10 ml) containing anisole (1.5 ml, 13.6 mmol, 50 equiv). The HF is removed in vacuo and the residue washed with ether, extracted into 0.1 M acetic acid and lyophilized to give a white solid, the compound of formula X.

EXAMPLE 3

L-Glutaminyl-L-alanyl-glycyl-L-glutamyl-L-serine(IX)

The remainder of the tetrapeptide resin (2.168 mmol) is coupled by 1 cycle in which steps (j) and (k) of Example 1 are replaced with Boc-Gln-ONp (3.18 g, 8.67 mmol, 4 equiv.) in 25 ml DMF for 24 hr to give the pentapeptide resin.

A 1.0 g portion (0.271 mmol) of the pentapeptide resin is cleaved at 0° for 45 min. with HF (210 ml) containing anisole (1.5 ml, 13.6 mmol, 50 equiv). The HF is removed in vacuo and the residue washed with ether, extracted into 0.1 M acetic acid and lyophilized to give a white solid, the compound of formula IX.

EXAMPLE 4

L-Lysyl-L-glutaminyl-L-alanyl-glycyl-L-glutamyl-L-serine (VIII)

The remainder of the pentapeptide resin (1.897 mmol) is coupled by 1 cycle with N-Boc-Nα-Cbz-L-Lys-OH (2.88 g, 7.59 mmol, 4 equiv.) to give the hexapeptide resin.

1.0 g portion (0.271 mmol) of the hexapeptide resin is cleaved at 0° for 45 min. with HF (~10 ml) containing anisole (1.5 ml, 13.6 mmol, 50 equiv.) The HF is removed in vacuo and the residue washed with ether, extracted into 0.1 M acetic acid and lyophilized to give a white solid, the compound of formula VIII.

EXAMPLE 5

L-Glutamyl-L-lysyl-L-glutaminyl-L-alanyl-glycyl-L-glutamyl-Lserine (VII)

The remainder of the hexapeptide resin (1.626 mmol) is coupled by 1 cycle with Boc-Glu(OBzl)-OH (2.92 g, 8.67 mmol, 4 equiv.) to give the heptapeptide resin.

A 1.0 g portion (0.271 mmol) of the heptapeptide resin is cleaved with HF (~10 ml) at 0° for 45 min containing anisole (1.5 ml, 13.6 mmol, 50 equiv.). The HF is removed in vacuo and the residue washed with ether, extracted into 0.1 M acetic acid and lyophilized to give a white solid, the compound of formula VII.

EXAMPLE 6

L-glutaminyl-L-glutamyl-L-lysyl-L-glutaminyl-L-alanyl-glycyl-L-glutamyl-L-serine (VI)

The remainder of the heptapeptide resin (1.355 mmol) is coupled by 1 cycle in which steps (j) and (k) of Example 1 are replaced with Boc-Gln-ONp (1.99 g, 5.42 mmol, 4 equiv.) in 25 ml DMF for 24 h to give the octapeptide resin.

A 1.0 g portion (0.271 mmol) of the octapeptide resin is cleaved with HF (~10 ml) at 0° for 45 min. containing anisole (1.5 ml, 13.6 mmol, 50 equiv.). The HF is removed in vacuo and the residue washed with ether, extracted into 0.1 M acetic acid and lyophilized to give a white solid, the compound of formula VI.

EXAMPLE 7

L-Glutamyl-L-glutaminyl-L-glutamyl-L-lysyl-L-glutaminyl-L-alanyl-glycyl-L-glutamyl-L-serine (V)

The remainder of the octapeptide resin (1.084 mmol) is coupled by 1 cycle with Boc-Glu(OBzl)-OH (1.46 g, 4.336 mmol, 4 equiv.) to give the nonapeptide resin.

A 1.0 g portion (0.271 mmol) of the nonapeptide resin was cleaved at 0° for 45 min. with HF (~10 ml) containing anisole (1.5 ml, 13.6 mmol, 50 equiv.). The HF is removed in vacuo and the residue washed with ether, extracted into 0.1 M acetic acid and lyophilized to give a white solid, the compound of formula V.

EXAMPLE 8

L-Isoleucyl-L-glutamyl-L-glutaminyl-L-glutamyl-L-lysyl-L-glutaminyl-L-glutamyl-L-alanyl-glycyl-L-glutamyl-L-serine (IV)

The remainder of the nonapeptide resin (0.813 mmol) is coupled by 1 cycle with Boc-Ile-OH (752 mg, 3.252 mmol, 4 equiv.) to give the decapeptide resin.

A 1.0 g portion (0.271 mmol) of the decapeptide resin is cleaved at 0° for 45 min. with HF (~10 ml) containing anisole (1.5 ml, 13.6 mmol, 50 equiv.). The HF is removed in vacuo and the residue washed with ether, extracted into 0.1 M acetic acid and lyophilized to give a white solid, the compound of formula IV.

EXAMPLE 9

L-Threonyl-L-isoleucyl-L-glutamyl-L-glutaminyl-L-glutamyl-L-lysyl-L-glutaminyl-L-alanyl-glycyl-L-glutamyl-L-serine (III)

The remainder of the decapeptide resin (0.542 mmol) is coupled by 1 cycle with Boc-Thr(Bzl)-OH (670 mg, 2.168 mmol, 4 equiv.) to give the undecapeptide resin.

A 1.0 g portion (0.271 mmol) of the undecapeptide resin is cleaved at 0° for 45 min with HF (~10 ml) containing anisole (1.5 ml, 13.6 mmol, 50 equiv.). The HF is removed in vacuo and the residue washed with ether, extracted into 0.1 M acetic acid and lyophilized to give a white solid, the compound of formula III.

EXAMPLE 10

L-Glutamyl-L-threonyl-L-isoleucyl-L-glutamyl-L-glutaminyl-L-glutamyl-L-lysyl-L-glutaminyl-L-alanyl-glycyl-L-glutamyl-L-serine (II)

The remainder of the undecapeptide resin (0.271 mmol) is coupled by 1 cycle with Boc-Glu (OBzl)-OH (365 mg, 1.084 mmol, 4 equiv.) to give the dodecapeptide resin. This material is cleaved at 0° for 45 min. with HF (~10 ml) containing anisole (1.5 ml, 13.6 mmol, 50 equiv.). The HF is removed in vacuo and the residue washed with ether, extracted into 0.1 M acetic acid and lyophilized to give a white solid, the compound of formula II.

EXAMINE 11

L-Glutaminyl-L-alanyl-glycyl-L-glutamyl-L-seryl-L-aspartyl-L-alanyl-L-lysyl-L-threonine (XII)

A solution of 3.678 g (11.9 mmol) of Nα-Boc-O-benzyl-L-threonine, 1.50 ml (10.7 mmol) of triethylamine in 25 ml of obsolute ethanol is reacted with 10.0 g (11.9 mmol) of chloromethylated copolystyrene-1% divinylbenzene (1.19 mmol Cl/g resin). The reaction mixture is worked up by the procedure outlined in Example 10. Amino acid analysis shows the resin to contain 0.312 mmol of Thr/g.

Solid phase peptide synthesis is carried out as described in Example 10. A 10.0 g portion of the TFA-H-Thr(Bzl)-O-Resin (3.12 mmol) is coupled respectively by 1 cycle each with Boc-Lys(Cbz)-OH (4.742 g, 12.48 mmol, 4 equiv.) and Boc-Ala-OH (2.360 g, 12.48 mmol, 4 equiv.) to give the tripeptide resin.

A 1.0 g portion (0.312 mmol) of the tripeptide resin is coupled respectively by 1 cycle each with Box-Asp (OBzl)-OH (403 mg, 1.248 mmol, 4 equiv.), Boc-Ser(Bzl)-OH (368 mg, 1.248 mmol, 4 equiv.), Boc-Glu(OBzl)-OH (421 mg, 1.248 mmol, 4 equiv.), Boc-Gly-OH (218 mg, 1.248 mmol, 4 equiv.) and Boc-Ala-OH (236 mg, 1.248 mmol, 4 equiv.). A final cycle in which steps (j) and (k) of Example 1 are replaced with Boc-Gln-ONp (458 mg, 1.248 mmol, 4 equiv.) in 25 ml DMF for 24 hr to give the nonapeptide resin. This product is cleaved at 0° for 45 min. with HF (~10 ml) containing anisole (1.72 ml, 15.6 mmol, 50 equiv.). The HF is removed in vacuo and the residue washed with ether, extracted into 0.1 M acetic acid and lyophilized to give a white solid, the compound of formula XII.

EXAMPLE 12

L-Glutaminyl-L-alanyl-glycyl-L-glutamyl-L-seryl-L-asparayinyl-L-alanyl-L-lysyl-L-threonine (XIII)

Another 1.0 g portion (0.312 mmol) of the tripeptide resin from example XII is coupled respectively by 1 cycle in which steps (j) and (k) of Example 1 are replaced by Boc-Asn-ONp ONp (441 mg, 1.248 mmol, 4 equiv.) in 25 ml DMF for 24 hr. This is followed by further respective couplings of 1 cycle each with Boc-Ser(Bzl)-OH (368 mg, 1.248 mmol, 4 equiv.), Boc-Glu(OBzl)-OH (218 mg, 1.248 mmol, 4 equiv.), Boc-Gly-OH (218 mg, 1.248 mmol, 4 equiv.) and Boc-Ala-OH(236 mg, 1.248 mmol, 4 equiv.). A final cycle in which steps (j) and (k) were replaced with Boc-Gln- ONp (458 mg, 1.248 mmol, 4 equiv.) in 25 ml DMF for 24 hr gives the nonapeptide resin. This product is cleaved at 0° for 45 min. with HF (210 ml) containing anisole (1.72 ml, 15.6 mmol, 50 equiv.). The HF is removed in vacuo and the residue washed with ether, extracted into 0.1 M acetic acid and lyophilized to give a white solid, the compound of formula XIII.

EXAMPLE 13

N-Acetyl-L-glutaminyl-seriosyl-glycyl-L-glutamyl-L-seryl-L-aspartyl-L-alanyl-L-lysyl-L-threonine (XIV)

Another 1.0 g portion (0.312 mmol) of the tripeptide resin from example XII is coupled respectively by 1 cycle each with Bor-Asp (OBzl)-OH (403 mg, 1.248 mmol, 4 equiv.), Boc-Ser (Bzl)-OH (368 mg, 1.248 mmol, 4 equiv.), Boc-Glu(OBzl)-OH (421 mg, 1.248 mmol, 4 equiv.), Boc-Gly-OH (218 mg. 1,248 mmol, 4 equiv.), and Boc-Sar-OH (236 mg, 1.248 mmol, 4 equiv.). A final cycle in which steps (j) and (k) of Example 1 are replaced with Ac-Gln-ONp (386 mg, 1.248 mmol, 4 equiv.) in 25 ml DMF for 24 hr gives the nonapeptide resin. This product is cleaved at 0° for 45 min. with HF (~10 ml) containing anisole (1.72 ml, 15.6 mmol, 50 equiv.). The HF is removed in vacuo and the residue washed with ether, extracted into 0.1 M acetic acid and lyophilized to give a white solid, the compound of formula XIV.

EXAMPLE 14

N-Acetyl-L-glutaminyl-sarcosyl-glycyl-L-glutamyl-L-seryl-L-asparyinyl-L-alanyl-L-lysyl-L-threonine (XV)

Another 1.0 g portion (0.312 mmol) of the tripeptide resin from example XII is coupled by 1 cycle in which steps (j) and (k) of Example 1 are replaced by Boc-Asn-ONp (441 mg, 1.248 mmol, 4 equiv.) in 25 ml DMF for 24 hr. This is followed by respective couplings with Boc-Ser(Bzl)-OH (368 mg, 1.248 mmol, 4 equiv.), Boc-Glu(OBzl)-OH (421 mg, 1.248 mmol, 4 equiv.), Boc-Gly-OH (218 mg, 1.248 mmol, 4 equiv.) and Boc-Sar-OH(236 mg, 1.248 mmol, 4 equiv.). A final cycle in which steps (j) and (k) of Example 1 are replaced with Ac-Gln-ONp (386 mg, 1.248 mmol, 4 equiv.) in 25 ml DMF for 24 hr gives the nonapeptide resin. This product is cleaved at 0° for 45 min. with HF (~10 ml) containing anisole (1.72 ml, 15.6 mmol, 50 equiv.). The HF is removed in vacuo and the residue washed with ether, extracted into 0.1 M acetic acid and lyophilized to give a white solid, the compound of formula XV.

EXAMPLE 15

L-Glutaminyl-L-alanyl-glycyl-L-glutamyl-L-seryl-L-aspartyl-L-glutamyl-L-isoleucyl-L-threonyl-L-alanyl-L-lysyl-L-threonine (XVI)

Another 1.0 g portion (0.312 mmol) of the tripeptide resin from example XII is coupled by 1 cycle each with Boc-Thr(Bzl)-OH (386 mg, 1.248 mmol, 4 equiv.), Boc-Ile-OH (289 mg, 1.248 mmol, 4 equiv.), Boc-Glu(OBzl)-OH (421 mg, 1.248 mmol, 4 equiv.), Boc-Asp(OBzl)-OH (403 mg, 1.248 mmol, 4 equiv.), Boc-Ser(Bzl-OH (368 mg, 1.248 mmol, 4 equiv.), Boc-Glu(OBzl)-OH (421 mg, 1.248 mmol, 4 equiv.), Boc-Gly-OH (218 mg, 1.248 mmol, 4 equiv.) and Boc-Ala-OH (236 mg, 1.248 mmol, 4 equiv.). A final cycle in which steps (j) and (k) of Example I are replaced with Boc-Gln-ONp (458 mg, 1.248 mmol, 4 equiv.) in 25 ml DMF for 24 hr gives the dodecapeptide resin. This product is cleaved at 0° for 45 min. with HF (~10 ml) containing anisole (1.72 ml, 15.6 mmol, 50 equiv.). The HF is removed in vacuo and the residue washed with ether, extracted into 0.1 M acetic acid and lyophilized to give a white solid, the compound of formula XVI.

EXAMPLE 16

Part A

The in vivo effect of thymosin fractions, i.e. thymosin $\beta_3$ (designated HCA-thymosin $\beta_3$), thymosin $\beta_4$ (designated HCA-thymosin $\beta_4$), thymosin fraction 5 (designated HCA-thymosin fr 5), compound of formula VI (designated HCA-synthetic C8 $\beta_4$) and compound of formula XVI (designated HCA-synthetic C12 $\beta_3$, on TdT activity in thymocytes of hydrocortisone acetate (HCA) treated C57B1/6J mice was assayed and determined according to the method of Hu, et al., 38, 1079 (1979).

For TdT activity determination [(following the Hu et al method (supra)], a 1.25 mg HCA injection per animal was carried out at day zero (0). Each injection was followed by daily treatment of the animal with the thymosin fractions (supra) or controls, i.e. no HCA and HCA-saline, for eleven (11) consecutive days. The increase in TdT specific activity (nmoles of dGTP incorporated per $10^8$ thymocytes per hour) over that of HCA-saline treated animals was determined, the data compiled in columns 1–4 of Table 2.

Part B

The in vivo effect of thymosin fractions (supra) on restoration of splenic mitogenic responses in HCA suppressed C57B1/6J mice was assayed and determined by the following method.

Splenic lymphocytes were removed sterilly, placed in plastic petri dishes containing RPMI 1640 (with 25 mM HEPES buffer, 100 µ/ml penicillin, 100 µg/ml streptomycin and 2mM L-glutamine) and a 64-mesh stainless steel wire screen. Single cell suspensions were obtained by further passage through a 25 GA needle. The cells were washed twice, counted using a Coulter Counter Model A and suspended to give a concentration of $6 \times 10^6$ leukocytes/ml. Cultures were prepared in flat bottom 96 well microtiter plates by placing 0.10 ml of the cell suspension into each well plus 0.05 ml 20% heat inactivated fetal calf serum (FCS) (resulting in $6 \times 10^5$ cells/well in 5% FCS final). Control cultures received 0.05 ml of RPMI 1640, and the stimulated cultures received 0.025 ml of RPMI 1640 containing various concentrations of thymosin and 0.025 ml of various concentrations of PHA-P (Difco, Detroit, Michigan), Con-A (Calbiochem, Oxnard, California), PWM (GIBCO, Grand Island, New York) or E. coli LPS (Difco, Detroit, Michigan) all made up in RPMI 1640. Cultures were pulsed by adding 1 uCi tritiated thymidine, 1.9 Ci/mM (Schwartz/Mann, Orangeburg, New Jersey), in 0.02 ml of RPMI 1640 8 hours before culture termination. Cultures were harvested utilizing a Multiple-Automated Sample Harvester (Microbiological Associates, Bethesda, Maryland). The resulting filter spots were dried and placed in glass liquid scintillation minivials to which was added 1 ml of scintillation cocktail. The vials were stoppered and the tritiated thymidine incorporation analyzed by scintillation spectrophotometry on an LKB liquid scintillation counter to provide Con A (cpm) and PHA-P (cpm). Processing of the data and necessary statistical tests were performed on a Wang 700 C Advanced Programming Calculator (Wang Labs, Tewksbury, Massachusetts) and are compiled in columns 1-2 and 5-6 of Table 2.

ered insignificant. The date from these experiments are compiled in Table 3.

TABLE 2

IN VIVO EFFECT OF THYMOSIN $\beta_3$ AND $\beta_4$ AND C-TERMINAL SYNTHETIC ANALOGUES ON THYMOCYTE TdT ACTIVITY AND RESTORATION OF SPLENIC MITOGENIC RESPONSES IN HYDROCORTISONE ACETATE (HCA) SUPPRESSED C57B1/6 MICE

| Treatment* | Amount/ Injection | TdT Specific Activity | TdT % Increase | Mitogens Con A (cpm) | Mitogens PHA—P (cpm) |
|---|---|---|---|---|---|
| Normal (no HCA) | — | 8.9 | — | 210,000 | 30,000 |
| HCA—Saline | — | 6.4 | — | 86,000 | 12,000 |
| HCA—Thymosin Fr.5 | 100 μg | 10.0 | + 57 | 175,000 | 35,000 |
| HCA—Thymosin $\beta_4$ | 1 μg | 8.8 | + 38 | 125,000 | 10,000 |
| HCA—Synthetic C8 $\beta_4$ | 10 μg | 7.6 | + 19 | 140,000 | 11,000 |
| HCA—Thymosin $\beta_3$ | 1 μg | 9.7 | + 52 | 120,000 | 27,000 |
| HCA—Synthetic C12 $\beta_3$ | 10 μg | 8.2 | + 28 | 110,000 | 65,000 |

*6 to 8 mice/group.

EXAMPLE 17

The standardized Macrophage Migration Inhibitory Factor (MIF) assay for natural thymosin $\beta_4$, synthetic thymosin $\beta_4$, compounds of formula XVI, (designated C12 $\beta_3$), formula VI (designated C8 $\beta_4$), formula IV (designated C10 $\beta_4$), and formula VIII (designated C6 $\beta_4$) was performed following the method of Thurman, et al., Lymphokines and Thymic Hormones: Their Potential Utilization in Cancer Therapeutics, ed. by Goldstein and Chirigos, Raven Press, New York, pp 145-157 (1981).

Peritoneal exudate cells (PEC) from guinea pig were prepared in Hartley strain guinea pigs by injecting 20-30 ml of sterile mineral oil 3-5 days prior to the assay. On the day of the assay, the guinea pigs were anesthetized and injected i.p. with 50 ml of RPMI-1640. Following abdominal massage, the peritoneum was opened with a one inch incision in the umbilical region and the peritoneal fluids withdrawn. The peritoneal fluids were centrifuged at 200×g for 10 min and the pelleted cells resuspended in a small volume of RPMI for transfer to clean tubes. Following three more washes, the cells were resuspended, counted and adjusted to 45×106/ml for use.

In some experiments mouse PEC were used in place of guinea pig PEC. The mouse PEC were induced in BALB/c normal or nude mice by injecting 1 ml of mineral oil i.p. 3 days prior obtaining the cells by washing the peritoneum with 5 ml of RPMI 1640. In some experiments macrophage-like cell lines, WEHI-3 and FC-1, were used in place of PEC. The WEHI-3 cells migrate and have been reported to respond to migration inhibitory factor (MIF). Likewise, the FC-1 cells are also migratory and respond to MIF.

The nonspecific MMI assay did not involve antigen and measured the direct effect various polypeptides had on macrophage inhibition. The percent nonspecific inhibition (PNSI) was calculated as:

$$PNSI = 100 - \left[ \frac{\text{Area (thymosin preparation)}}{\text{Area } (RPMI)} \times 100 \right]$$

If the means of the replicates for various polypeptides were not significantly different from the mean of the RPMI control by Student's t-Test (p<0.05), the inhibition was considered insignificant. Percent nonspecific inhibition of migration of less than 20% was also considered insignificant.

TABLE 3

Effect of thymosin $\beta_4$ and its synthetic C-terminal fragments on inhibition of macrophage migration

| Thymosin Preparation | Concentration (nmoles/ml) | PNSI |
|---|---|---|
| Natural thymosin $\beta_4$ | 0.5 | 37.6 |
|  | 0.05 | 29.2 |
|  | 0.005 | 23.1 |
| Synthetic thymosin $\beta_4$ | 0.5 | 30.3 |
|  | 0.05 | 25.9 |
|  | 0.005 | 25.0 |
| C12 $\beta_3$ Gln—Ala—Gly—Glu—Ser—Asp—Glu—Ile—Thr—Ala—Lys—Thr | 0.5 | 30.2 |
|  | 0.05 | 29.7 |
|  | 0.005 | 24.7 |
|  | 0.0005 | 23.5 |
| C8 $\beta_4$ Gln—Glu—Lys—Gln—Ala—Gly—Glu—Ser | 0.5 | 24.1 |
|  | 0.05 | 25.4 |
|  | 0.005 | 27.0 |
|  | 0.0005 | 5.5 |
| C10 $\beta_4$ Ile—Glu—Gln—Glu—Lys—Gln—Ala—Gly—Glu—Ser | 0.5 | 21.6 |
|  | 0.05 | 18.8 |
|  | 0.005 | 10.7 |
|  | 0.0005 | −5.3 |
| C6 $\beta_4$ Lys—Gln—Ala—Gly—Glu—Ser | 0.5 | 18.3 |
|  | 0.05 | 15.2 |
|  | 0.005 | −5.1 |
|  | 0.0005 | 3.1 |

We claim:
1. A peptide of the formula

R-Gly-Glu-Ser-R<sub>1</sub> wherein R represents H-Q, Q-Ala-, Q-Gln-Ala, Q-Glu-Lys-Gln-Ala, Q-Gln-Glu-Lys-Gln-Ala-, Q-Glu-Gln-Glu-Lys-Gly-Ala, Q-Ile-Glu-Gln-Glu-Lys-Gin-Ala, Q-Thr-Ile-Glu-Gln-Glu-Lys-Gln-Ala-, Q-Glu-Thr-Ile-Glu-Gln-Glu-Lys-Gin-Ala, or Q-Gln-Sar-wherein Q represents H or acyl; and R<sub>1</sub> represents -OH, -A-C or -A-B-C wherein A represents Asp or Asn, B represents -Glu-Ile-Thr- and C represents -Ala-Lys-Thr-Oh.
and the pharmaceutically acceptable acid or base addition salts thereof.

2. A peptide according to claim 1 which is H-Glu-Thr-Ile-Glu-Gln-Glu-Lys-Gln-Ala-Gly-Glu-Ser-OH.

3. A peptide according to claim 1 which is H-Ile-Glu-Gln-Glu-Lys-Gln-Ala-Gly-Glu-Ser-OH.

4. A peptide according to claim 1 which is H-Gln-Glu-Lys-Gln-Ala-Gly-Glu-Ser-OH.

5. A peptide according to claim 1 which is H-Gln-Ala-Gly-Glu-Ser-OH.

6. A peptide according to claim 1 which is H-Ala-Gly-Glu-Ser-OH.

7. A peptide according to claim 1 which is H-Gly-Glu-Ser-OH.

8. A peptide according to claim 1 which is H-Gln-Ala-Gly-Glu-Ser-Asp-Ala-Lys-Thr-OH.

9. A peptide according to claim 1 which is H-Gln-Ala-Gly-Glu-Ser-Asn-Ala-Lys-Thr-OH.

10. A peptide according to claim 1 which is $CH_3CO$-Gln-Sar-Gly-Glu-Ser-Asp-Ala-Lys-Thr-OH.

11. A peptide according to claim 1 which is $CH_3CO$-Gln-Sar-Gly-Glu-Ser-Asn-Ala-Lys-Thr-OH.

12. A peptide according to claim 1 which is H-Gln-Ala-Gly-Glu-Ser-Asp-Glu-Ile-Thr-Ala-Lys-Thr-OH.

13. A method for stimulating the production of TdT positive prothymocytes, for inhibiting macrophage migration, or restoring immune responses of steroid suppressed mammalian subject, said method comprising administering to said subject an effective amount of a peptide of claim 1.

* * * * *

UNITED STATES PATENT AND TRADEMARK OFFICE
CERTIFICATE OF CORRECTION

PATENT NO. : 4,395,404
DATED : July 26, 1983
INVENTOR(S) : Teresa L. K. Low and Allan L. Goldstein It is certified that error appears in the above-identified patent and that said Letters Patent are hereby corrected as shown below:

Column 12, line 50, claim 1, "H-Q" should be: Q

Column 1, line 49, "H-Q" should be: Q

Signed and Sealed this

Twenty-ninth Day of May 1984

[SEAL]

Attest:

GERALD J. MOSSINGHOFF

Attesting Officer         Commissioner of Patents and Trademarks